United States Patent [19]

Leüsner et al.

[11] 4,389,496
[45] Jun. 21, 1983

[54] THIXOTROPIC FORMULATIONS OF SILICONE PASTES FOR IMPRESSIONS OF TEETH AND MUCOUS MEMBRANE

[75] Inventors: Bernhard Leüsner, Leverkusen; Hans-Hermann Schulz, Leichlingen; Reiner Voigt; Michael Walkowiak, both of Leverkusen, all of Fed. Rep. of Germany

[73] Assignee: Bayer Aktiengesellschaft, Leverkusen, Fed. Rep. of Germany

[21] Appl. No.: 320,623

[22] Filed: Nov. 12, 1981

Related U.S. Application Data

[63] Continuation of Ser. No. 128,340, Mar. 7, 1980, abandoned.

[30] Foreign Application Priority Data

Mar. 17, 1979 [DE] Fed. Rep. of Germany ....... 2910560

[51] Int. Cl.$^3$ .............................................. C09K 3/00
[52] U.S. Cl. ..................................... 523/109; 106/35; 260/998.11; 433/214
[58] Field of Search ..................... 106/35; 260/998.11; 523/109; 433/48, 214

[56] References Cited

U.S. PATENT DOCUMENTS

| | | | |
|---|---|---|---|
| 3,082,527 | 3/1963 | Nitzsche | 32/17 |
| 3,792,147 | 2/1974 | Wohlfarth | 264/225 |
| 3,925,277 | 12/1975 | Lampe | 260/18 S |
| 4,007,153 | 2/1977 | Smith | 523/109 |
| 4,035,453 | 7/1977 | Hittmair | 523/109 |
| 4,174,338 | 11/1979 | Goller | 260/37 SB |
| 4,222,983 | 9/1980 | August | 523/109 |
| 4,261,758 | 4/1981 | Wright | 106/287.12 |

FOREIGN PATENT DOCUMENTS

826738 1/1960 United Kingdom .
1033903 6/1966 United Kingdom .

*Primary Examiner*—Allan Lieberman
*Assistant Examiner*—Patricia Short
*Attorney, Agent, or Firm*—Sprung, Horn, Kramer & Woods

[57] ABSTRACT

The invention relates to thixotropic formulations of silicone pastes for the production of exact impressions of teeth and mucous membrane.

12 Claims, No Drawings

THIXOTROPIC FORMULATIONS OF SILICONE PASTES FOR IMPRESSIONS OF TEETH AND MUCOUS MEMBRANE

This is a continuation of application Ser. No. 128,340, filed Mar. 7, 1980, abandoned.

The present invention relates to thixotropic formulations of silicone pastes for the production of exact impressions of teeth and mucous membrane, and to such impressions of teeth and mucous membrane. These formulations consist of the base mixture in a two-component silicone rubber system which, in use, vulcanizes in the cold, the base mixture being combined with a catalyst/crosslinking agent mixture and the resulting mixture being crosslinked at room temperature after 2 to 5 minutes.

Cold-curing silicone rubber is increasingly used in dentristy as an impression composition for taking impressions of a jaw bearing teeth or a toothless jaw in the production of dentures. Depending on the indication, the material is used in the form of pastes of varying consistency, with which a curing agent is mixed before used. The transition from a pasty brushable consistency to the rubbery-elastic state takes place in the course of about 4 to 5 minutes at body temperature. After this time, the impression can be removed from the mouth without difficulty, as a result of the elasticity of the material, and from this a cast can be made, for example using gypsum, to product a working model.

The advantages of this silicone impression composition compared with gypsum, which was customary earlier, are the elasticity of the cured material and the fact that the cured material is unbreakable and can easily be separated from the jaw. Silicone impression pastes even have advantages compared with the alginates which are frequently used at present. They are not sensitive to loss of water, which can be the cause of shrinkage phenomena and is exhibited by these alginates, and the cast is more accurate. The dimensional stability of silicone impressions is outstanding, and is retained even when the impressions are stored in air for a long time (compare the book "Chemie und Technologie der Silikone" ("Chemistry and Technology of Silicones" by Walter Nell, Verlag Chemie, Weinheim, Bergstrasse, 4968 Chapter 400, 13.2.).

The most diverse fillers are used, depending on the consistency of the silicones impression compositions, and examples of fillers are: highly disperse silicic acids, calcium silicates, calcium carbonates, pumice, talc, calcium sulphate, quartz powder and cristobalite powder.

In the case of mobile impression compositions with viscosities of about 10,000 mPa.s, particularly light fillers have to be used, in order to avoid demixing. It is thus quite natural that such compositions display certain thixotropic characteristics. However, this effect has never consciously been intensified in order to obtain a paste, as in the present invention, which has a low viscosity during mixing with the catalyst/crosslinking component, during application to the impression holder or when being forced out of the syringe, and in the mouth of the patient displays an increase in viscosity, as a result of the thixotropic effect, which prevents further flow of the paste after application.

According to the present invention there is provided a thixotropic formulation of silicone paste for the production of impressions of teeth and mucous membrane which essentially consists of a silicone oil, an organic thixotropic agent and calcium silicate.

The calcium silicate which is incorporated in the formulation has a selected surface area. In a particular composition, for example, the paste can have viscosities of between 100,000 and 10,000 m Pa.s (all viscosities being measured in a Brookfield viscometer at 23° C.), and is intended for use in the field of low-viscosity impression compositions for correction impressions. As a result of having a different composition, more highly thixotropic paste formulations with viscosities of between 800,000 and 30,000 mPa.s (measured, as above, in a Brookfield viscometer) are used for the production of mucous membrane impressions.

Moreover, depending on the indication, the thixotropic character can be increased further to a viscosity greater than 350,000 mPa.s, preferably 1,000,000 to 350,000 mPa.s, so that it is possible to dispense with the edge shaping with, for example, kneadable silicone impression compositions, which is usually carried out, for example to produce extension areas when taking impressions of a toothless lower jaw.

The silicone paste, which is to be mixed with a catalyst/crosslinking component and thereby cured, consists of preferably (a) 50 to 90% by weight of a silicone oil containing terminal hydroxyl groups e.g. polydimethylsiloxane of the formula

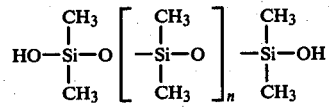

having a viscosity between 500 and 20,000 mPa.s (particularly 2000 mPa.s; (in the formula n depends on the viscosity as follows: 500 mPa.s: n=250; 2000 mPa.s: n=500; 20,000 mPa.s: n=950); preferably (b) 1–15% by weight of an organic thixotropic agent e.g. a non-ionic organic thixotropic agent, such as glycerine monostearatepolyglycol ether of the formula

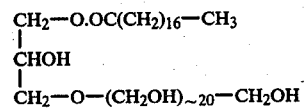

and preferably (c) 5 to 50% by weight of calcium silicate ($CaO.SiO_2$) having, for example, a specific surface area, measured by the BET method of 20–100 $m^2/g$, more preferably 35–65 $mg^2/g$.

The present invention further relates to an impression of teeth and mucous membrane which has been formed by applying to said teeth a thixotropic formulation of the present invention incorporating a catalyst/crosslinking component.

The silicone oils employed are most preferably polydiorganosiloxanes which contain hydroxyl groups. These siloxanes can be substituted by any of the known monovalent hydrocarbon radicals or halogenated hydrocarbon radicals, for example by alkyl radicals with 1 to 8 carbon atoms, such as methyl, ethyl, propyl, butyl, pentyl, hexyl, heptyl and octyl, by alkenyl radicals with 1 to 8 carbon atoms, such as vinyl, allyl and butenyl, by halogenated alkyl radicals, such as chloropropyl and 3,3,3-trifluoropropyl, by cycloalkyl radicals, such as cyclobutyl, cyclopentyl and cyclohexyl, and further-more by aromatic radicals, such as phenyl, tolyl, xylyl and naphthyl, or halogenated aromatic radicals, such as chlorophenyl and chloronaphthyl, and by alkylaryl radicals, such as benzyl and phenylethyl. A particularly preferred silicone oil is a polydimethylsilioxane which contains terminal hydroxy groups.

In addition to the diorganosiloxy units ($R_2SiO$), the diorganopolysiloxanes can also contain triorganosiloxy units ($R_3SiO_{0.5}$), monoorganosiloxy units ($RSiO_{1.5}$) and unsubstituted silicon dioxide units ($SiO_2$).

The viscosity of the silicone oils employed is preferably between 500 and 20,000 mPa.s, and is more preferably about 2,000 mPa.s.

The organic thixotropic agents are preferably anionic, cationic or non-ionic emulsifiers. Non-ionic emulsifiers are more preferably employed. As described in Ullmanns Enzyklopädie der technischen Chemie (Ullmann's Encyclopaedia of Industrial Chemistry), Volume 10, Chapter: Emulsionen (Emulsions), 4th edition, Verlag Chemie GmbH, Weinheim, these non-ionic emulsifiers include fatty acid esters of alcohols (N 101), ethylene glycol (N 102), polyethylene glycol (N 103), propylene glycol (N 104), glycerol, polyglycerol (N 105), sorbitol (N 106), pentaerythritol (N 107), glycerol esters (N 108) and sucrose (N 109), as well as fatty amines and fatty acid amides (N 200), polyglycerol ethers (N 300), for example polyglycerol ethers of fatty acid esters, such as glycerides, or sorbitol esters (N 304) and finally polypropylene glycol ethers (N 400).

The calcium silicate employed should preferably have a specific surface area (measured by the BET method) of 20–100 $m^2/g$, more preferably 35–65 $m^2/g$.

The base mixture consisting of the silicone oil, organic thixotropic agent and calcium silicate is, in use, combined with a catalyst/crosslinking agent mixture and the resulting mixture is cured at room temperature for between 2 and 5 minutes. Crosslinking substances which are preferably employed are silicic acid O-esters, polysilicic acid esters or substituted silane crosslinking agents. Examples of silicic acid O-esters are silicic acid O-methyl, O-ethyl, O-n-propyl, O-isopropyl, O-chloroethyl, O-octyl, O-allyl, O-hexenyl, O-cyclohexyl, O-phenyl, O-benzyl or O-chlorophenyl ester and mixed O-alkyl esters of silicic acid, such as silicic acid O-dimethyl O-diethyl ester. Examples of the polysilicic acid esters formed by partial hydrolysis and condensation or by heating the above-mentioned silicic acid O-esters are methyl polysilicate, ethyl polysilicate and n-propyl polysilicate.

Examples of silane crosslinking agents are methyltrimethoxysilane, methyltriethoxysilane, ethyltrimethoxysilane, ethyltriethoxysilane, n-propyltrimethoxysilane, n-propyltriethoxysilane, phenyltrimethoxysilane, phenyltriethoxysilane and methyltriacetoxysilane.

The amount of crosslinking compound to be added is preferably 0.1 to 10 parts by weight per 100 parts by weight of polyorganosiloxane.

All catalysts which promote silanol condensation, the reaction of silanol with alkoxy or with other groups which can be hydrolysed by water and the hydrolysis of alkoxy, or other groups, bonded to silicon can be used as curing catalysts in the process according to the invention.

Examples of these catalysts are the metal salts of organic monocarboxylic acids, which can contain as the metal lead, tin, zirconium, antimony, iron, cadmium, calcium, barium, manganese, bismuth or titanium, such as dibutyl-tin dilaurate, dibutyl-tin diacetate, tin-II octoate, lead laurate, cobalt naphthenate, tetrabutyl titanate, tetraoctyl titanate and tetraisopropyl titanate. Further examples are amines, such as n-hexylamine and cyclohexylamine, and amine salts, such as hexylamine hydrochloride, butylamine acetate and guanidine di-ethylhexoate. Carboxylic acid salts of tin are preferred catalysts. The amount of curing catalyst added is preferably between 0.1 and 10%, relative to the organopolysiloxane employed.

Surprisingly, it has been found that the combination of organic thixotropic agent, for example glycerol monostearate polyglycol ether, with calcium silicate which has a specific surface area of about 50 $m^2/g$ displays a particularly powerful thixotropic effect. Thus, in a particular composition it is possible that the "low-viscosity" pastes can be metered out as a ribbon for correction impressions, that is to say have a high viscosity, assume a low viscosity during mixing with the crosslinking/catalyst component and during application, so that the paste can flow into narrow carcks, and then becomes more highly viscous again and is thus prevented from flowing away from the point of application.

In another composition of the base mixture, an impression of the surface of the mucous membrane is made in exact detail, on the one hand, as a result of the thixotropic effect, and on the other hand, in the static muscle phase, the impression composition is prevented from the flowing away which was customary in the case of previous low-viscosity impression compositions which were not thixotropic formulations.

The agents, or low-viscosity silicone pastes, customary hitherto have the disadvantage that, after application, they flow on in the mouth and in certain circumstances drip from the point of application. As a result, retching is frequently triggered off by the composition flowing away into the pharyngal cavity, and discomfort is thus caused to the patient. In many cases, the impression thereby becomes useless.

The thixotropic formulations according to the invention on the one hand prevent the paste dripping from the point of application, but on the other hand are also distinguished by good flow properties under low pressure, so that the surfaces of which an impression is to be made can be reproduced exactly.

The present invention will be illustrated in more detail with the aid of the following Examples in which Examples 1 to 3 relate to the preparation of base mixture, Example 4 relates to the preparation of catalyst/crosslinking component and Examples 5 to 7 relate to the preparation of vulcanised base mixture.

EXAMPLE 1

550 g of a polydimethylsiloxane which contains terminal hydroxyl groups and has a viscosity of about 2,000 mPa.s at 23° C., and 450 g of calcium silicate with a specific surface area of $50 \pm 15$ $m^2/g$ (measured by the BET method) are mixed in a planetary mixing and kneading machine for 30 minutes.

619 g of the polydimethylsiloxane which contains terminal hydroxyl groups and has a viscosity of about 2,000 mPa.s are stirred with 25 g of a glycerol monostearate polyglycol ether at 70° C. in a second mixing tank of the planetary mix and kneading machine, 356 g of the silicone/calcium silicate mixture prepared above are added, the mixture is stirred at 70° C. for 15 minutes and mixing is then continued for 30 minutes, whilst cooling with cold water.

EXAMPLE 2

490 g of a polydimethylsiloxane which contains terminal hydroxyl groups and has a viscosity of about 2,000 mPa.s at 23° C. are stirred with 30 g of a glycerol monostearate polyglycol ether at 70° C. in a mixing tank of the planetary mixing and kneading machine, and after adding 478 g of the silicone/calcium silicate mixture mentioned in Example 1, the temperature is kept at 70° C. for 15 minutes and mixing is then continued for 30 minutes, whilst cooling with cold water.

EXAMPLE 3

835 g of a polydimethylsiloxane containing terminal hydroxyl groups are mixed with 35 g of a hydrogenated castor oil at 90° C. in a mixing tank of a planetary mixing, and kneading machine, the mixture is then cooled with cold water, whilst stirring, and 130 g of a calcium silicate with a specific surface area of about 50 $m^2/g$ (measured by the BET method) are then stirred in. After a subsequent stirring time of 30 minutes, the paste is transferred to a homogeniser.

EXAMPLE 4

300 g of tetraethoxysilane and 300 g of dibutyltin dilaurate are stirred at 120° C. in a 1 l flask with a stirrer and nitrogen connection.

EXAMPLES 5 TO 7

In each case 6 g of the base mixture form Examples 1, 2 or 3 are mixed intimately with 0.25 g of the crosslinking/catalyst component from Example 4 for 30 seconds. After one minute, some of the mixture is transferred to a small metal cap; the surface is smoothed over and the metal cap containing the vulcanisation mixture is introduced into a thermostatically controlled waterbath at 37° C. The Shore A hardness of the vulcanisates is in each case measured after 4'30", 6', 8' and 10'.

The processing properties are tested with another portion of the mixture of base mixture and crosslinking-/catalyst component by carrying out the so-called "digital test". For this test, some of the mixture is taken between the thumb and forefinger, which are moved against one another until the vulcanisation mixture "tears." The result of the digital test is the time from the start of the mixing to the "tearing."

The following table contains viscosity data for the base mixtures and vulcanisation results for the mixtures obtained therefrom.

| Base mixtures from Example | 1 | 2 | 3 |
|---|---|---|---|
| Viscosity in mPa.s at 23° C., measured with a Brookfield RVT viscometer | | | |
| Spindle | 6 | 7 | 6 |
| 0.5 revolution/minute | 90,000 | 800,000 | 102,000 |
| 1.0 revolution/minute | 63,000 | 560,000 | 76,800 |
| 2.5 revolutions/minute | 41,200 | 312,000 | 52,800 |
| 5.0 revolutions/minute | 31,000 | 204,000 | 33,600 |
| 10.0 revolutions/minute | 24,000 | 142,000 | 22,400 |
| 20.0 revolutions/minute | 19,000 | 94,000 | 15,800 |
| 50.0 revolutions/minute | 14,800 | 62,000 | 11,300 |
| Base mixture from Example | 1 | 2 | 3 |
| Crosslinking/catalyst component from Example | 4 | 4 | 4 |
| Amount of base mixture in g | 6.00 | 6.00 | 6.00 |
| Amount of crosslinking/catalyst component in g | 0.25 | 0.25 | 0.25 |
| Digital test | 2'55" | 2'35" | 2'45" |
| Shore A hardness | | | |
| after 4½ minutes | 17 | 21 | 16 |
| after 6 minutes | 23 | 31 | 25 |
| after 8 minutes | 29 | 34 | 30 |
| after 10 minutes | 31 | 36 | 33 |

What is claimed is:

1. A thixotropic silicone paste for the production of impressions, said paste consisting essentially of
   (a) 50–90%, based on the weight of the paste, of a silicone oil with terminal hydroxyl groups;
   (b) 1–15%, based on the weight of the paste, of an organic thixotropic agent; and
   (c) 5–50% of calcium silicate,
   wherein
   (i) said calcium silicate has a specific surface area of 20 to 100 $m^2/g$ (measured by the BET method) and
   (ii) said thixotropic agent is selected from the group consisting of hydrogenated castor oil and polyglycol ethers of glycerides.

2. A paste according to claim 1 wherein said thixotropic agent is glycerol monostearate polyglycol ether.

3. A paste according to claim 1 in which the silicone oil has a viscosity of 500 to 20,000 mPa.s at 23° C.

4. A paste according to claim 1 or 2 in which the silicone oil has a viscosity of about 2,000 mPa.s at 23° C.

5. A paste according to claim 1 in which the calcium silicate has a specific surface area of 35 to 65 $m^2/g$ (measured by the BET method).

6. A paste according to claim 1 in which the calcium silicate has a specific area of about 50 $m^2/g$ (measured by the BET method).

7. A paste according to claim 1, which has a viscosity between 100,000 and 10,000 mPa.s at 23° C. and is suitable for correction impressions.

8. A paste according to claim 1 which has a viscosity between 800,00 and 30,000 mPa.s and is suitable for mucous membrane impressions.

9. A paste according to claim 1 having a viscosity over 350,000 mPa.s and suitable for kneading to produce extension areas.

10. A paste according to claim 9 which has a viscosity between 350,000 and 1,000,000 mPa.s at 23° C.

11. A paste according to claims 1 or 2 which is crosslinked with a crosslinking/catalyst component consisting of a silicic acid O-ester, a polysilicic acid ester or a substituted silane crosslinking agent and a metal salt of an organic monocarboxylic acid.

12. An impression of teeth and mucous membrane which has been formed by applying to said teeth and mucous membrane a paste as claimed in claim 1 incorporating a catalyst/crosslinking component.

* * * * *